United States Patent [19]

Andersen

[11] Patent Number: 5,451,212
[45] Date of Patent: Sep. 19, 1995

[54] BUMPER RETENTION DEVICE

[75] Inventor: Erik Andersen, Gurnee, Ill.

[73] Assignee: Corpak, Inc., Wheeling, Ill.

[21] Appl. No.: 184,560

[22] Filed: Jan. 21, 1994

[51] Int. Cl.6 .................. A61M 5/32; A61M 25/00
[52] U.S. Cl. .................. 604/174; 604/178; 604/280
[58] Field of Search .......... 604/174, 175, 178, 264, 604/280, 256

[56] References Cited

U.S. PATENT DOCUMENTS

| | | | |
|---|---|---|---|
| 2,735,432 | 2/1956 | Hudson | 128/DIG. 26 X |
| 3,648,703 | 3/1972 | Manker | 128/DIG. 26 X |
| 3,782,388 | 1/1974 | Page | 128/DIG. 26 X |
| 4,148,319 | 4/1979 | Kasper et al. | |
| 4,393,873 | 7/1983 | Nawash et al. | |
| 4,834,712 | 5/1989 | Quinn et al. | |
| 4,834,713 | 5/1989 | Suthanthiran | |
| 4,863,438 | 9/1989 | Gauderer et al. | |
| 4,900,306 | 2/1990 | Quinn et al. | |
| 4,944,732 | 7/1990 | Russo | |
| 4,959,055 | 9/1990 | Hillyer | |
| 5,007,900 | 4/1991 | Picha et al. | 604/106 |
| 5,017,188 | 5/1991 | Marten et al. | 604/178 |
| 5,026,352 | 6/1991 | Anderson | 604/178 |
| 5,092,850 | 3/1992 | Buma | |
| 5,098,405 | 3/1992 | Peterson et al. | 604/247 |
| 5,125,897 | 6/1992 | Quinn et al. | |
| 5,263,944 | 11/1993 | Vidal et al. | 604/256 |
| 5,267,969 | 12/1993 | Hirsch et al. | 604/174 |
| 5,267,970 | 12/1993 | Chin et al. | 604/175 |
| 5,305,742 | 4/1994 | Styers et al. | 128/207.17 |
| 5,336,203 | 8/1994 | Goldhardt et al. | 604/247 |

Primary Examiner—John D. Yasko
Assistant Examiner—Adam J. Cermak
Attorney, Agent, or Firm—Wallenstein & Wagner, Ltd.

[57] ABSTRACT

The present invention relates generally to a device for securing a tube, such as a medical catheter or feeding tube, at the site of a body opening. More specifically, the invention is directed to a bumper retention device for retaining a feeding tube in an angular fixation externally against the skin of a patient, so as to prevent slippage, dislodgement, or unnecessary migration of the feeding tube into the stomach, small intestine or other internal body cavity of a patient. The bumper retention device may be used with a conventional catheter or feeding tube and a conventional retention bar. The bumper retention unit comprises a retention stem portion connected to a loop portion. The loop portion is placed around the outer diameter of the feeding tube and when the tube is bent, the stem portion is inserted into an end aperture of the retention bar so that the tube is retained at an approximately 90° angle.

8 Claims, 2 Drawing Sheets

FIG. 1
FIG. 2
FIG. 3
FIG. 4
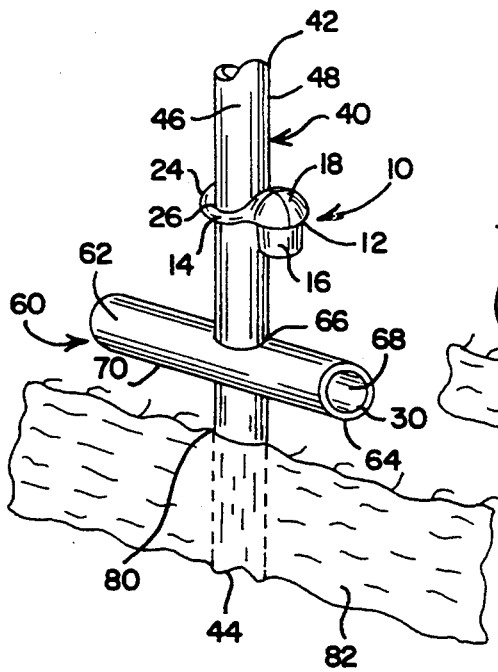
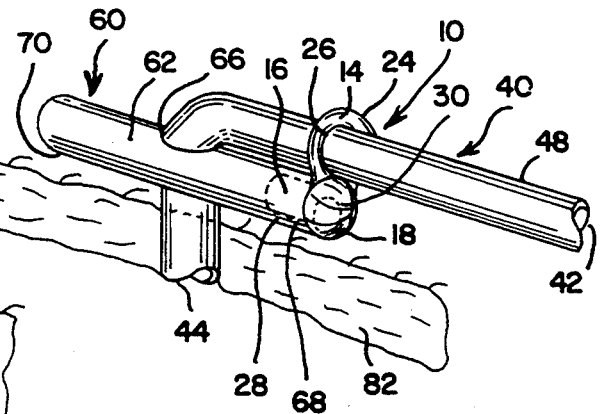
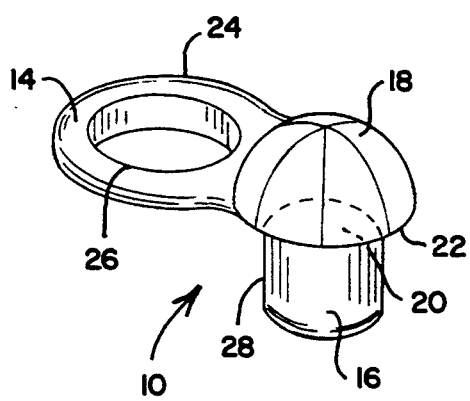
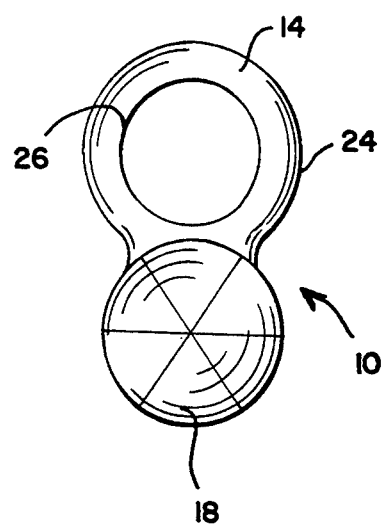

BUMPER RETENTION DEVICE

DESCRIPTION

TECHNICAL FIELD

The present invention relates generally to a device for securing a tube, such as a medical catheter or feeding tube, at the site of a body opening. More specifically, the invention is directed to a bumper retention device for retaining a feeding tube in an angular fixation externally against the skin of a patient, so as to prevent slippage, dislodgement, and unnecessary migration of the tube.

BACKGROUND OF THE INVENTION

The use of various indwelling medical catheter tubes, especially feeding tubes, is well known in the medical art. Feeding tubes, such as percutaneous enteral gastrostomy (PEG) tubes or jejunostomy tubes, are used in patients requiring long-term nutritional support. Such tubes may be left within the body for lengthy periods of time, in part, due to their construction of biocompatible materials such as silicone, which material has an ability to remain soft and flexible for long periods of time within the body. In addition, the silicone construction provides for a tube having a smooth surface with a very low coefficient of friction. However, such surface smoothness may have the disadvantage of causing the silicone feeding tube to become very slippery when in contact with body fluids. Thus, the positioning of a tube through an abdominal or gastric wall opening or other body opening is accompanied with the risks of unwanted or accidental slippage of the tube, dislodgement or removal of the tube, or inward migration of the tube into the stomach or other body cavity. It is important that the enteral feeding tube, upon insertion through the body opening or surgically formed feeding stoma, be maintained in a relatively stationary and concentric position during enteral feeding, so as not to cause discomfort or improper delivery of fluids to the patient.

In an attempt to minimize slippage, dislodgement and migration of medical catheters and feeding tubes, others have employed external retention devices. For example, U.S. Pat. No. 4,959,055 to Hillyer discloses a percutaneous tube retainer having an end segment and annular edge which grips the tube outer wall surface to prevent tube slippage. U.S. Pat. No. 5,007,900 to Picha et al., discloses a percutaneous endoscopic gastrostomy device comprising a catheter with a resilient T-bar at one end which bears against the skin of a patient. U.S. Pat. No. 5,092,850 to Buma discloses a catheter with an adjustable external locking bolster similar to a retention disc or bar which can be locked in place to prevent tube slippage. U.S. Pat. No. 4,834,713 to Suthanthiran discloses a catheter button which is inserted into the end of a catheter tube in order to secure the tube.

Although these patents recognize problems associated with securely holding a catheter in place, they have deficiencies. These devices are directed to retention bar devices and devices for insertion into the end of a catheter and do not uniquely fix a catheter or feeding tube in an angular position. Rather, the catheters or feeding tubes of the above discussed patents are typically positioned in an upright or substantially upwardly straight manner, and thus, the tubes may slide through the retention T-bar and further migrate inwardly. In addition, there may be a problem with slippage and migration of the tube in those devices disclosing an end closure of the tube when such end closure is not in use.

U.S. Pat. No. 4,834,712 to Quinn et al., discloses a device for angular fixation of a delivery or drainage tube having sleeve and flange portions. However, the device of Quinn et al., is comprised of two uniquely shaped parts which are difficult to manufacture and high in cost. Furthermore, when in situ, this device is very rigid and is not considered very low profile.

Thus, there is a need for a bumper retention device that holds a catheter or feeding tube securely in place and in an angular fixation, that prevents the tube from slipping through a retention bar, that minimizes removal or dislodgement by a patient, that prevents migration of the tube into the stomach or other body cavity, that causes little, if any, irritation to the skin of a patient, and that is easy to mold, manufacture, assemble, and use.

The present invention overcomes the deficiencies associated with the devices discussed above by providing such a novel bumper retention device having all of the above advantages, and that, in application, can be used with a conventional feeding tube or catheter and a conventional feeding tube retention bar.

SUMMARY OF THE INVENTION

The present invention is directed to a bumper retention device for use with a conventional catheter or feeding tube and a conventional retention bar. The bumper retention device of the present invention retains a catheter or feeding tube in an external angular fixation at about skin level, so as to prevent inward tube migration into the stomach or other body cavity, eliminate tube slippage and prevent dislodgement or removal by a patient.

Specifically, the device is directed to a bumper retention unit comprising a retention stem portion connected to a loop portion. In use, the loop portion is placed around a conventional feeding tube or catheter, and the bumper retention device is moved downwardly along the tube to a point above and near the top surface of the retention bar. The desired point to position the loop portion along the tube is preferably approximately equal in distance to the distance from the end of the retention bar to the point of insertion of the tube through the retention bar.

The retention stem portion of the bumper retention device comprises a stem and a cap. Once the bumper retention device is at the desired position along the tube, the tube is bent at the point that it is inserted through the retention bar, and the tube is bent to the side until it is parallel to and in contact with the retention bar so that the tube is positioned at approximately a 90° angle. The stem is inserted into an end aperture of the conventional retention bar and securely fixed within the aperture, so as to completely close off such aperture and so as to retain the tube in angular fixation for a desired period of time.

Thus, it is a principal aspect of the present invention to provide a relatively simple, external, skin level, bumper retention device to retain a feeding tube, catheter, and the like, in angular fixation for long-term internal feedings and the like.

It is another aspect of the present invention to provide a device with novel retention means for retaining the inner end of a feeding tube or catheter within the stomach or other body cavity of a patient and the outer end of the feeding tube or catheter near or flush against the skin of a patient.

It is another aspect of the present invention to provide a novel retention means which positions and retains a tube through an abdominal or gastric wall opening or other body opening with minimal, if any, unwanted or accidental slippage of the tube, dislodgement or removal of the tube, or inward migration of the tube into the stomach or other body cavity.

It is another aspect of the present invention to provide a novel bumper retention device which, once it is secured in place to the retention bar, does not easily slide along the tubular shaft of the feeding tube or catheter.

It is another aspect of the present invention to provide a bumper retention device that causes little, if any, irritation to the skin of a patient.

It is another aspect of the present invention to provide a bumper retention device made of substantially rigid polyethylene material, or the like, that is easily and economically manufactured, permanently assembled prior to use, safe, convenient and easy to use.

Other advantages and aspects of the present invention will become apparent upon reading the following description of the drawings and the detailed description of the invention and preferred embodiment of the invention.

BRIEF DESCRIPTION OF THE DRAWINGS

FIG. 1 is a perspective view of a bumper retention unit according to the invention, shown in use with a conventional feeding tube and a conventional retention bar;

FIG. 2 is a perspective view of the bumper retention unit of FIG. 1, shown in use with a conventional feeding tube and a conventional retention bar, wherein a retention stem of the bumper retention unit is inserted into an end aperture of the retention bar to retain the feeding tube in angular fixation;

FIG. 3 is a perspective view of a bumper retention unit according to the invention;

FIG. 4 is a top view of the bumper retention unit of FIG. 3 according to the invention;

DETAILED DESCRIPTION OF THE INVENTION

Figure 5:
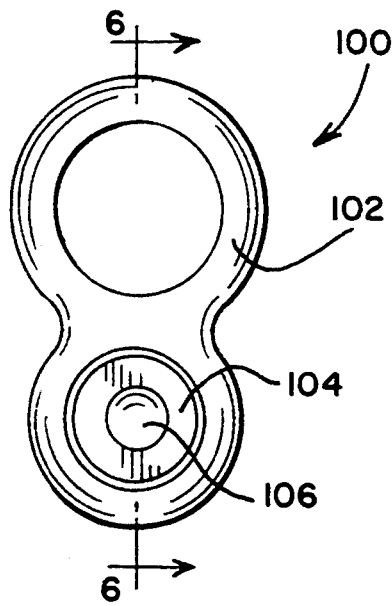
FIG. 5 is a bottom view of another embodiment of a bumper retention unit according to the invention.

While this invention is susceptible of embodiment in different forms, there is shown in the drawings and will herein be described in detail, a preferred embodiment of the invention. The present disclosure is to be considered as an exemplification of the principles of the invention and is not intended to limit the broad aspect of the invention to the embodiment illustrated.

Referring now to the drawings, FIG. 1 shows an embodiment of a bumper retention unit or device of the present invention, generally referenced by numeral 10. The bumper retention unit 10 is generally used in conjunction with a conventional feeding tube 40, and in particular, with percutaneous enteral gastrostomy (PEG) feeding tubes, replacement gastrostomy tubes, or jejunostomy tubes for retaining the tube 40 in place. The tube 40 is generally circular in cross-section and resiliently deformable, has a proximal end 42 and a distal end 44, a tubular shaft 46, and an outer tube diameter 48. The tube 40 extends externally upwardly from an opening 80 in the skin 82 of a patient in order to deliver, extract, and carry fluids or gases into and out of the patient. It is also preferable to use the bumper retention device 10 in conjunction with a conventional retention device, such as a retention bar 60. The retention bar 60 is typically cylindrical in shape with a hollow interior and a generally circular cross-section. The retention bar 60 of FIG. 1 has a top surface 62, a first end 64, a central opening 66 in which the tube 40 is inserted, and an end aperture 68.

The bumper retention unit 10 is generally used with the tube 40 and the retention bar 60 in an external manner. The bumper retention unit 10 comprises a retention stem portion 12 connected to a loop portion 14. The bumper retention unit 10 is made of a rigid or substantially rigid material, preferably polyethylene. It will be appreciated that the construction of the bumper retention unit 10 is not limited to polyethylene material and that any suitable rigid or substantially rigid material may be used, such as polypropylene. The retention stem portion 12 comprises a stem 16 and a cap 18. The stem 16 is preferably substantially cylindrical in shape with a generally circular cross-section. The stem 16 may be solid in construction or have a substantially hollow interior (see FIGS. 6, 8). The cap 18 may be substantially rounded or hemispherical in shape (see FIG. 6) or substantially flat (see FIG. 8). The bumper retention unit 10 may be constructed with the stem 16, the cap 18, and the loop portion 14 being of varying sizes depending on the size of the feeding tube 40 or catheter used with the bumper retention unit 10. Preferably, the loop portion 14 has an inner loop diameter 26 that is sufficient in size to fit snugly around the outer tube diameter 48 of the feeding tube 40. In general, it is preferable to have the inner diameter of the loop portion of the bumper retention device of the present invention correspond in size to the outer diameter or French size of the feeding tube or catheter used with the bumper retention device. The French scale unit is typically used for denoting the diameter size of tubes, such as gastrostomy and catheter tubes, where each French unit is roughly equivalent to 0.33 millimeters (mm) in diameter, i.e., 3 French is equal to about 1 mm.

Referring to FIG. 3, a top end surface 20 of the stem 16 is attached to a bottom end surface 22 of the cap 18. The loop portion 14 is also attached to both the bottom end surface 22 and to the cap 18 and projects outwardly from the side of the cap 18. The loop portion 14 has an outer loop diameter 24, as well as the inner loop diameter 26. The inner loop diameter 26 is of a size sufficient to fit snugly around the outer tube diameter 48 of the feeding tube 40.

The inner loop diameter 26 of the bumper retention device 10 is initially aligned with and placed over the proximal end 42 of the feeding tube 40 (FIG. 1). The loop portion 14 is placed around the outer tube diameter 48 of the feeding tube 40 and the entire bumper retention device 10 is slidably moved downwardly along the tube 40 to a point above and near the retention bar top surface 62. The desired position of placement of the loop portion 14 along the tube 40 is preferably approximately equivalent in distance to the distance from the first end 64 of the retention bar 60 to the retention bar central opening 66, that is, the opening 66 where the tube 40 is inserted through the retention bar 60. Although the loop portion 14 of the bumper retention device 10 is designed to fit snugly over the outer tube diameter 48 of the feeding tube 40, the bumper retention device 10 may be movably adjusted along the tube 40 both in a downward and upward direction.

FIG. 2 shows the bumper retention unit 10 of the present invention, in use, to retain the tube 40 in angular fixation. Preferably, the tube 40 is fixed at approximately a 90° angle. Once the bumper retention device 10 is at the desired position along the tube 40, the tube 40 is bent at about the point the tube 40 is inserted through the central opening 66 of the retention bar 60, and the tube 40 is bent to the side until it is substantially parallel to, and in contact with or substantially near, the top surface 62 of the retention bar 60, so that the tube 40 is preferably at approximately a 90° angle. The stem 16 is inserted into the end aperture 68 of the retention bar 60 and securely fixed within the end aperture 68, so as to completely close off the end aperture 68 (FIG. 1), and so as to retain the tube 40 in angular fixation for a desired period of time. The stem 16 has an outer stem diameter 28 which is slightly larger than a retention bar inner diameter 30, so that when the stem 16 is inserted into the end aperture 68, a substantially tight interference fit is formed between the stem 16 and the retention bar 60, by radially expanding the retention bar 60 slightly.

In use, the retention bar bottom surface 70 is positioned in abutment to or flush with the skin 82 of a patient. Because the cap 18 of the stem portion 12 is flush with the first end 64 of the retention bar 60, the bumper retention unit 10 is less likely to cause undue irritation or discomfort to a patient when used in conjunction with the feeding tube 40.

Thus, in use, the bumper retention device 10 retains the feeding tube 40 within the stomach or other body cavity of a patient with minimal, if any, unwanted or accidental slippage of the tube 40, dislodgement or removal of the tube 40, or inward migration of the tube 40 into the stomach or other body cavity. In addition, once the bumper retention device 10 is secured in place to the retention bar 40, the bumper retention device 10 is not easily movable along the tubular shaft of the feeding tube 40.

The bumper retention device 10 is easily and economically manufactured, permanently assembled prior to use, safe, convenient and easy to use.

FIG. 3 shows a perspective view of the preferred embodiment of the bumper retention unit 10 of the present invention. Although the preferred embodiment is shown, it will be appreciated that the construction of the bumper retention unit 10 is not limited to this embodiment, and variations of the shape and size of the device may be used with the present invention.

FIG. 4 shows a top view of the bumper retention unit 10 of the present invention. The loop portion 14 is of a size sufficient to snugly fit around the outer tube diameter 48 of the feeding tube 40.

Figure 6:
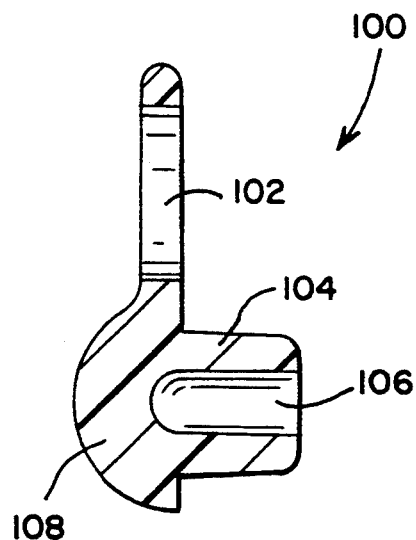
FIG. 6 is a cross-sectional side view taken along line 6—6 of FIG. 5, of the bumper retention unit of FIG. 5 according to the invention.

Another embodiment of a bumper retention unit 100 of the present invention is shown in FIGS. 5 and 6. FIG. 5 shows a bottom view of the bumper retention unit 100. The bumper retention unit 100 comprises a ring portion 102 and a stem portion 104. In this embodiment, the stem portion 104 has a central hollow portion 106, thus decreasing the amount of materials needed to manufacture this particular embodiment. FIG. 6 shows a cross-sectional side view taken along line 6—6 of FIG. 5, of the bumper retention unit according to the invention. A cap 108 is rounded and hemispherical in shape.

Figure 7:
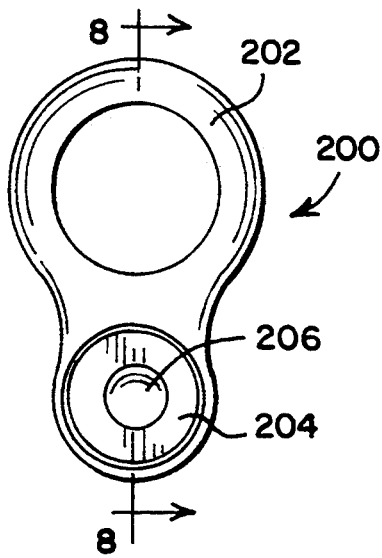
FIG. 7 is a bottom view of another embodiment of a bumper retention unit according to the present invention; and, FIG. 8 is a cross-sectional side view taken along line 8—8 of FIG. 7, of the bumper retention unit of FIG. 7 according to the invention.
Figure 8:
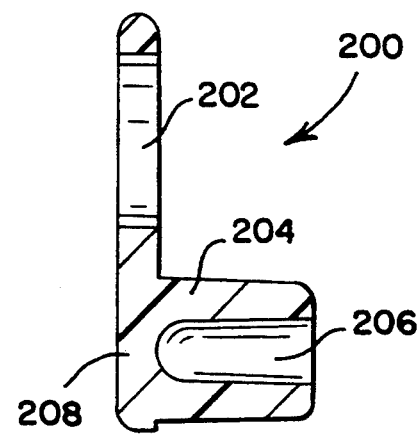

Yet another embodiment of a bumper retention unit 200 of the present invention is shown in FIGS. 7 and 8. FIG. 7 shows a bottom view of the bumper retention unit 200. The bumper retention unit 200 comprises a ring portion 202 and a stem portion 204. In this embodiment, the stem portion 204 is made with a central hollow portion 206, thus decreasing the amount of materials needed to manufacture this particular embodiment. FIG. 8 is a cross-sectional side view taken along line 8—8 of FIG. 7, of the bumper retention unit 200 of FIG. 7. In this embodiment, a cap 208 is flat on top rather than rounded, thus, again decreasing the amount of materials used in manufacturing this embodiment.

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention, should not be limited to such details.

What is claimed is:

1. A system for enteral feeding of a patient comprising:
    a tube used for the delivery or extraction of fluids or gases into or from said patient, said tube having a distal end, a proximal end, and a tubular shaft;
    a retention bar having a central opening through said bar and an end aperture, said tube being inserted through said central opening; and,
    a bumper retention unit connecting the tube and the retention bar for retaining said tube in angular fixation with respect to the retention bar, said bumper retention unit having a loop portion attached to a stem portion, said loop portion being dimensioned for placement around said tubular shaft of said tube and being movably adjusted to a position along said tubular shaft, said stem portion of said bumper retention unit being inserted into said end aperture of said retention bar, so as to retain said tube in angular fixation.

2. The system of claim 1 wherein said loop portion has an inner loop diameter and an outer loop diameter, said inner loop diameter being of a size sufficient to fit substantially tightly around an outer tube diameter of said medical tube.

3. The system of claim 1 wherein said retention bar end aperture defines an inner diameter, said stem portion comprises a stem and a cap, said stem having an outer diameter of sufficient size to form a tight interference fit with said inner diameter of said retention bar.

4. The system of claim 3 wherein said cap is substantially round in shape.

5. The system of claim 3 wherein said cap is substantially flat in shape.

6. A system for the delivery or extraction of fluids or gases into or from a patient, the system comprising:
    a medical tube;
    a retention bar; and,
    means detachably and reattachably connecting the medical tube and retention bar for maintaining a desired angular fixation between the medical tube and the retention bar.

7. The system of claim 6 wherein the means for maintaining a desired angular fixation comprises a retention stem portion and a loop portion attached to the retention stem portion.

8. A method for retaining a medical tube in a fixed angular relationship with a retention bar comprising the steps of:

providing a resilient medical tube;

providing a retention bar having a central opening and an end aperture;

providing a bumper retention unit having a loop portion connected to a retention stem portion;

inserting the medical tube through the retention bar central opening;

bending the medical tube about a central portion of the medical tube;

placing the loop portion about the medical tube; and, inserting the retention stem portion into the retention bar end aperture.

* * * * *